United States Patent
Bellini et al.

(10) Patent No.: US 9,415,091 B2
(45) Date of Patent: Aug. 16, 2016

(54) METHOD FOR PREPARING BIOCOMPATIBLE AND BIODEGRADABLE BIOMATERIALS BASED ON COLLAGEN AND GRANULES OF HYDROXYAPATITE/β-TRICALCIUM PHOSPHATE FOR USE IN SURGERY, AND BIOMATERIALS THUS OBTAINED

(71) Applicant: Novagenit S.r.l., Mezzolombardo (IT)

(72) Inventors: Davide Bellini, Albignasego (IT); Edgardo Cremascoli, Milan (IT)

(73) Assignee: NOVAGENIT S.R.L., Mezzolombardo (IT)

( * ) Notice: Subject to any disclaimer, the term of this patent is extended or adjusted under 35 U.S.C. 154(b) by 56 days.

(21) Appl. No.: 14/249,456

(22) Filed: Apr. 10, 2014

(65) Prior Publication Data
US 2014/0314849 A1    Oct. 23, 2014

(30) Foreign Application Priority Data

Apr. 18, 2013  (IT) .............. MI2013A0636

(51) Int. Cl.
| A61K 9/00 | (2006.01) |
| A61L 27/58 | (2006.01) |
| A61L 27/24 | (2006.01) |
| A61L 27/12 | (2006.01) |
| A61K 38/39 | (2006.01) |
| A61L 27/46 | (2006.01) |

(52) U.S. Cl.
CPC ............ *A61K 38/39* (2013.01); *A61L 27/24* (2013.01); *A61L 27/46* (2013.01); *A61L 2430/24* (2013.01)

(58) Field of Classification Search
CPC ......... A61L 27/54; A61L 27/58; A61L 27/24; A61K 2300/00; A61K 33/42
See application file for complete search history.

(56) References Cited

U.S. PATENT DOCUMENTS

| 4,668,295 | A | * | 5/1987 | Bajpai ........................ 106/690 |
| 2004/0151751 | A1 | * | 8/2004 | Cooper ........................ 424/423 |
| 2009/0232875 | A1 | * | 9/2009 | Tampieri et al. ............ 424/444 |
| 2010/0160922 | A1 | * | 6/2010 | Liu et al. ...................... 606/92 |

FOREIGN PATENT DOCUMENTS

| CA | 2103728 A1 * | 8/1992 |
| GB | 2440721 A | 2/2008 |
| WO | 2006092718 A2 | 9/2006 |
| WO | 2011064724 A1 | 6/2011 |

OTHER PUBLICATIONS

International Search Report dated Dec. 16, 2013 for MI20130636.

* cited by examiner

*Primary Examiner* — Frederick Krass
*Assistant Examiner* — Tracy Liu
(74) *Attorney, Agent, or Firm* — Abelman, Frayne & Schwab

(57) ABSTRACT

The present invention relates to a method of preparing a composite biomaterial, essentially consisting of collagen in combination with granules of hydroxyapatite/β-tricalcium phosphate (HA/β-TCP), to be used in maxillofacial surgery, dentistry, aesthetic surgery and particularly in orthopedic surgery; the invention also relates to the biomaterial obtained by means of this method.

5 Claims, 2 Drawing Sheets

METHOD FOR PREPARING BIOCOMPATIBLE AND BIODEGRADABLE BIOMATERIALS BASED ON COLLAGEN AND GRANULES OF HYDROXYAPATITE/β-TRICALCIUM PHOSPHATE FOR USE IN SURGERY, AND BIOMATERIALS THUS OBTAINED

FIELD OF THE INVENTION

The present invention relates to a method for preparing a biomaterial, essentially consisting of collagen in combination with granules of hydroxyapatite/β-tricalcium phosphate (HA/β-TCP), and to the biomaterial thus obtained; the biomaterial finds application in several areas of surgery, such as maxillofacial surgery, dentistry, aesthetic surgery and particularly orthopedic surgery.

BACKGROUND ART

In modern surgery, wide use is made of implants, namely, the introduction into the body of materials that can replace damaged parts of the same; in particular, implants are very common for replacing bones or sections thereof, or for temporarily fill voids in the bone structure, that are to be afterwards replenished by the growth of fresh bone tissue. Examples of these surgery areas are the maxillofacial surgery, in which damaged parts of the face are reconstructed; dentistry, in which the implants are mainly directed to create a stable seat in the maxillar or mandibular bone for metal elements to which prostheses will then be fixed; aesthetic surgery, in which implants are mostly directed to fill wrinkles; and orthopedic surgery, in which the insertion of material into the damaged part has generally the function of providing a temporary substitute for natural tissues and a suitable substrate for their re-growth during the healing process (and possibly also a promoting effect for such re-growth).

In orthopedic surgery, a particularly challenging application is the treatment of articular lesions, because of the need of preserving the mobility of the part (which may be not an issue in other surgery areas), and because in many cases the damage to be repaired involves both bone and cartilage tissues.

The description that follows will refer mainly to orthopedic surgery, but the biomaterials described below are of general application, at least in the other surgery areas mentioned before.

Osteochondral lesions, i.e., affecting both the bone and the cartilage connected thereto, are the most serious ones in the typical classifications of cartilage defects; in the classification of defects according to Outerbridge, the osteochondral defect represents level IV, which is the maximum level in terms of severity of the lesion. These lesions were formerly treated only with the implant of metal prostheses, but more recently implant materials which are more similar to the tissues to be repaired or regenerated have been used, which have better expectations of success in the long run; in fact, especially in the case of younger patients, obtaining the regeneration of a new bone and cartilage tissue in the area of the lesion in a joint allows the affected patient to regain the original form of the joint, i.e. of perfect efficiency, and above all a repair tissue which is fully integrated with the circulatory system, the lymphatic system, and even with the nervous system. To this end, materials have been developed which form the so-called "scaffolds", i.e., supports having a three-dimensional structure on which the patient's repairing cells cling and migrate during the process of rehabilitating the space left by the osteochondral damage.

Products have long been known and used, which consist of or contain hydroxyapatite ($Ca_5(PO_4)_3OH$) and/or the crystalline form β of tricalcium phosphate ($Ca_3(PO_4)_2$), for the preparation of scaffolds useful for the bone tissue regeneration.

Hydroxyapatite (often referred to by the abbreviation HA in the field, which will be used hereafter) is a material with a high biomimetic attitude against the bone tissue, with a porosity very similar to that of the spongy tissue of the bone and capable of accommodating osteoblasts, thus allowing them to settle and transform into osteocytes; moreover, it has excellent biocompatibility, and when placed in direct contact with the bone it shows osteoconduction and osteointegration and, in the presence of bone growth induction factors, also osteoinduction. Moreover, this material is the main mineral constituent of the bones, being 60% of the calcified human skeleton, and is therefore a natural candidate for the production of bone prostheses or fillers. It has been produced synthetically since the 70s, using a sintering process (agglomeration of a powder at a temperature below its melting point), and has been used clinically for about 20 years. However, HA has a poor degradability by body fluids and is therefore resistant to in vivo absorption.

For the production of scaffolds for bone regrowth, HA is therefore used in a mixture with a second mineral component, the crystalline form β of tricalcium phosphate ($Ca_3(PO_4)_2$), commonly known as β-tricalcium phosphate or by its abbreviation β-TCP, which will be used hereafter. β-TCP has a faster resorption than HA, and therefore promotes the regrowth of the bone tissue. These mixtures, referred to in the field by the abbreviation HA/β-TCP, may have different ratios of the two components.

A variety of biocompatible and biodegradable materials consisting of HA/β-TCP for use in orthopedic surgery is known.

The product OpteMx® by Exactech (Gainesville, Fla., USA) is available as preformed parts (e.g. parallelepiped or cylindrical in shape) consisting of the porous HA/β-TCP composition only, and has osteogenesis and limited osteoinduction properties when mixed with bone marrow blood.

The product MasterGraft® by Medtronic (Minneapolis, Minn., USA), available in granules of the HA/β-TCP composition only, has osteoconduction properties.

However, these materials are very fragile and thus not flexible, and poorly suitable for use in case of bone lumens or surfaces which are irregular in shape.

In order to overcome the problem, HA/β-TCP mixtures can be filled into a flexible matrix; the matrix material must be such that the final composite retains biocompatibility features. Widely used to this purpose is collagen, the most important structural protein in the human body, forming molecular wires which strengthen the tendons and large, elastic sheets that support the skin and internal organs. Bones and teeth are made of mineral crystals added to collagen. Collagen is a relatively simple protein, consisting of three chains, each containing more than 1400 aminoacids, wrapped together in a triple narrow helix.

Several products are known on the market which consist of HA and/or β-TCP in a collagen matrix.

The product MasterGraft® Putty by Medtronic, having osteoconduction properties, is formed by the same granules as the product MasterGraft® mentioned above, evenly distributed in a bovine collagen matrix.

The product Integra Mozaik™ by Integra LifeSciences Corporation (Plainsboro, N.J., USA), with osteoconductive properties, consists of a mixture containing about 80% β-TCP and 20% collagen.

The product Collagraft® Bone Graft Matrix by Zimmer (Warsaw, Ind., USA) is sold in the form of strips made of HA/β-TCP in a collagen matrix, which when added to autogenic bone marrow blood promote the bone repair process.

Finally, the product Healos® by DePuy (Warsaw, Ind., USA) consists of a matrix of cross-linked collagen fibers coated with HA; this product, combined with marrow blood, offers an excellent environment for the proliferation and differentiation of osteoprogenitor cells.

In cases of lesions affecting both the bone and the cartilage, the healing of the cartilage lesion is promoted by collagen, while that of the bone by the mineral components; known products, wherein HA and/or β-TCP are evenly distributed in the collagen matrix, are not optimal for these complex lesions.

Patent application WO 2011/064724 A1 describes mono-, bi- or multi-layer biomimetic materials for use in orthopedic surgery, and the process for their production. The basic material described in this application is a bicomponent material made of the natural polymer collagen added with chitosan (a polymer obtained by basic deacetylation of chitin, the natural component of exoskeleton of crustaceans). The mono-layer biomimetic materials of this application are made of collagen-chitosan only. This bicomponent material contains between 30 and 90% (preferably 50-80%) by weight of collagen, the remainder being chitosan; the role of chitosan is said to be for favoring the fibration of the bicomponent material. The production process of this collagen-chitosan material is however rather complex, requiring a rather complex sequence of steps carried out at controlled and different pH values. This application also describes a double layer material, comprising a layer of the collagen-chitosan material only, and a second layer of the same polymers containing nano- or microdimensional crystals or granules of HA (the preferred size of these crystals or granules being between 30 nm and 10 μm). A double layer material is said to be useful for the healing of osteochondral lesions, and is used by contacting the polymers-only layer with the lesion area in the cartilage, and the layer containing HA with the lesion area in the bone tissue. These double layers are obtained by preparing the collagen-chitosan material according to the same complex process mentioned above, and in particular preparing a layer made of polymers only, a separate layer made of polymers loaded with the nano- or micro-crystals or granules of HA, and then joining the two layers separately produced. The double layer materials of this application, though more suitable for the treatment of osteochondral lesions than polymeric materials in which HA is uniformly distributed, are of cumbersome preparation, due to the complexity of the preparation of the bicomponent polymeric material, and the need of producing the two layers separately.

It is the object of the invention to overcome the problems still existing in the field, and in particular to provide a composite useful as a matrix for the regeneration of tissues in several areas of surgery, and in particular in orthopedic surgery for the treatment of lesions affecting both the bone tissue and the cartilaginous tissue at the same time.

SUMMARY OF THE INVENTION

This object is achieved by the present invention, which in a first aspect relates to a method for the production of composite materials consisting of hydroxyapatite and β-tricalcium phosphate in a collagen matrix, where hydroxyapatite and β-tricalcium phosphate are unevenly distributed in the collagen, which comprises the following steps:
a) in a container, preparing an aqueous solution of collagen at a concentration between 0.5% and 2% by weight;
b) distributing a layer of granules of hydroxyapatite/β-tricalcium phosphate having a size between 0.3 and 5 mm on the surface of the solution prepared in step a) and waiting for the deposition by gravity of said granules on the bottom of the layer of collagen;
c) cooling the product obtained in step b) to a temperature between −20 and −30° C.;
d) subjecting to lyophilization the product obtained in step c).

In a second aspect, the invention relates to the product obtained by the above-described method, which consists of a double-layer composite, where a first layer consists of collagen only and a second layer consists of granules of hydroxyapatite/β-tricalcium phosphate or aggregates thereof immersed in the collagen matrix.

DETAILED DESCRIPTION OF THE INVENTION

The product of the invention is particularly suitable for the treatment and regeneration of tissues in osteochondral lesions, having an area mineralized with granules of HA/β-TCP where bone cells will be localized, and a fibrous protein area (collagen), where cartilage cells of the same patient will migrate, thus finding their ideal environment for reproduction and generation of the extracellular matrix; this product may however be used also in other surgery areas, for instance in maxillofacial surgery, dentistry, and aesthetic surgery.

Figure 1:
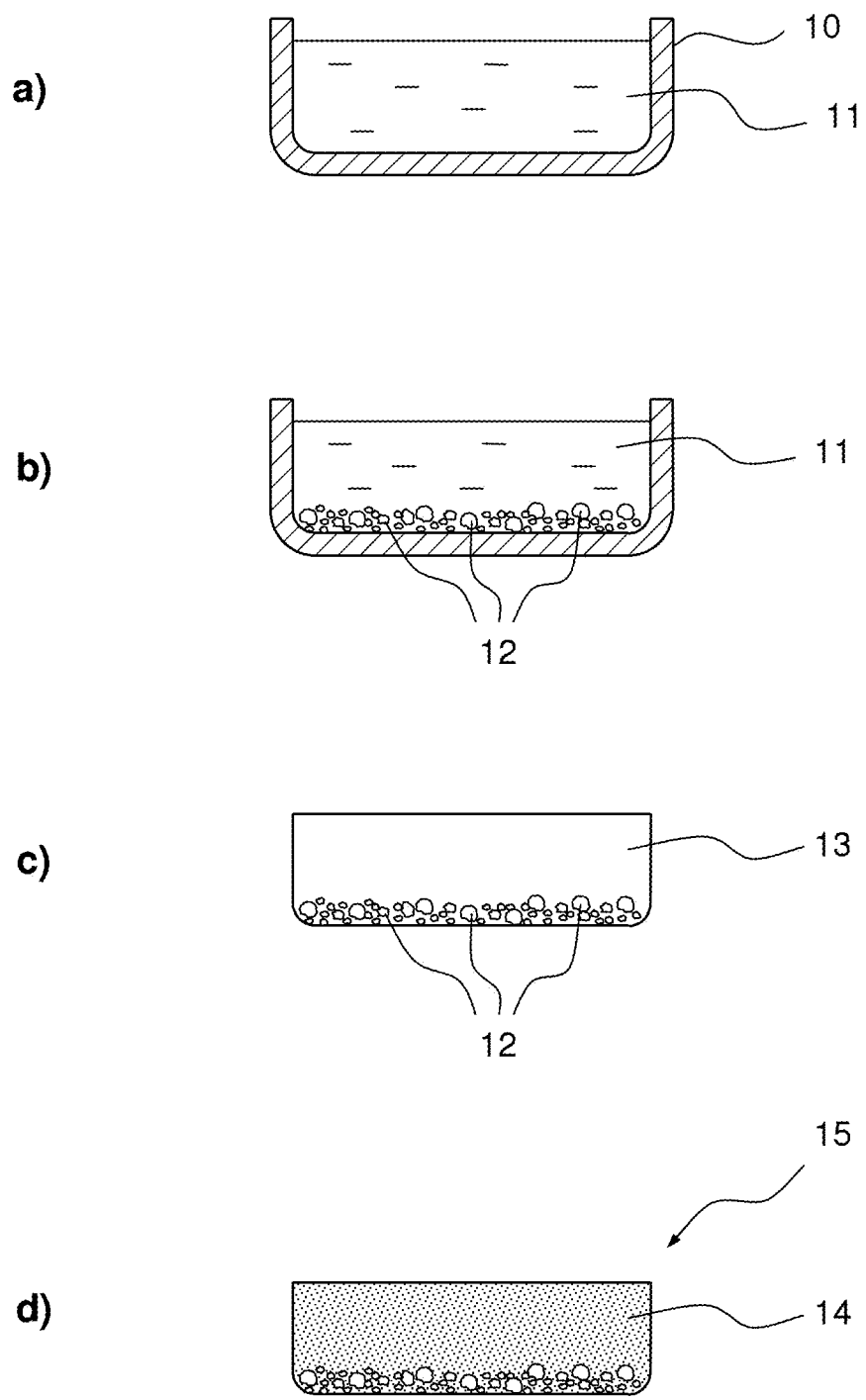
FIG. 1 diagrammatically shows the steps of the method of the invention.

According to a first aspect, the invention relates to a method for producing composites of HA/β-TCP and collagen, which comprises the above-mentioned steps a) to d). The method is described hereafter with reference to FIG. 1.

In step a) (FIG. 1.a), a solution 11 of collagen in water is prepared in a container 10. The collagen concentration in the solution can range from about 0.5 to 2% by weight, preferably about 1%; collagen is preferably obtained from equine tendon. In order to prepare the solution, the desired amount of collagen is added to water for injections (WFI) and the system is brought to a temperature of between about 60° C. and the hydrolysis temperature of collagen, which is about 75° C.; a temperature of between 60 and 65° C. is preferably used. The resulting solution appears as a very fluid, slightly opalescent liquid phase.

In step b) (FIG. 1.b), the solution 11 thus formed is kept at a temperature of between about 60 and 75° C., preferably at the same temperature at which it was produced in step a), and its free surface is covered with a layer of the granules of hydroxyapatite/β-tricalcium phosphate having a size of between 0.3 and 5 mm; the granules are shown in the Figure as a whole with reference numeral 12.

Working at these temperatures ensures that the solution remains fluid, so that the granules poured on the upper surface thereof can, by gravity, cross the thickness thereof to form a layer on the bottom of container 10.

For the purposes of the invention, the granules HA/β-TCP comprise the HA component in amounts of from 50 to 70%, preferably about 60%, by weight; the use of granules where HA is within the indicated range ensures optimal reabsorption timing in the body. These granules are commercially available and are manufactured and sold for example by Eurocoating S.p.A. of Ciré-Pergine (Trento) with the name OSPROLIFE™. Typically, smaller granules (up to about 1-1.2 mm) are single granules ("primary" granules), while larger ones, up to 5 mm, are derived from thermal aggregation in the production of primary granules. If desired, in view of the application, the granules may possibly be sieved to select the desired grain size fraction.

In step c) (FIG. 1.c), the solution added with the granules of HA/β-TCP is then cooled to a temperature between −20 and −30° C., thus causing the formation of a hydrogel 13, i.e. a gelatinous phase consisting of a network of collagen chains where the water of the starting solution is absorbed; the hydrogel has sufficient mechanical consistency and can be extracted from container 10; the lower layer of the hydrogel is formed by the deposit of the granules of HA/β-TCP surrounded by the hydrogel matrix, while the upper layer is formed by collagen hydrogel only.

Finally, in step d), the hydrogel is subjected to lyophilization by means of methods known in the field, in order to remove water, thus obtaining a dehydrated (lyophilized) hydrogel 14, (FIG. 1.d) which incorporates granules 12; the hydrogel consists of a highly elastic, composite double-layer matrix, with a clear and evident separation of the two components, collagen and granules of HA/β-TCP, where the inorganic part is perfectly integrated in the organic matrix; this particular structure gives rise to a synergy of behaviors that is the basis for achieving the desired results, leading to a higher yield than that obtained by the two elements taken separately.

Different from the teachings of WO 2011/064724 A1, thus, the method of the present invention allows to produce easily, as the direct product of the method, a double-layer composite material especially tailored for the treatment of osteochondral lesions.

Figure 2:
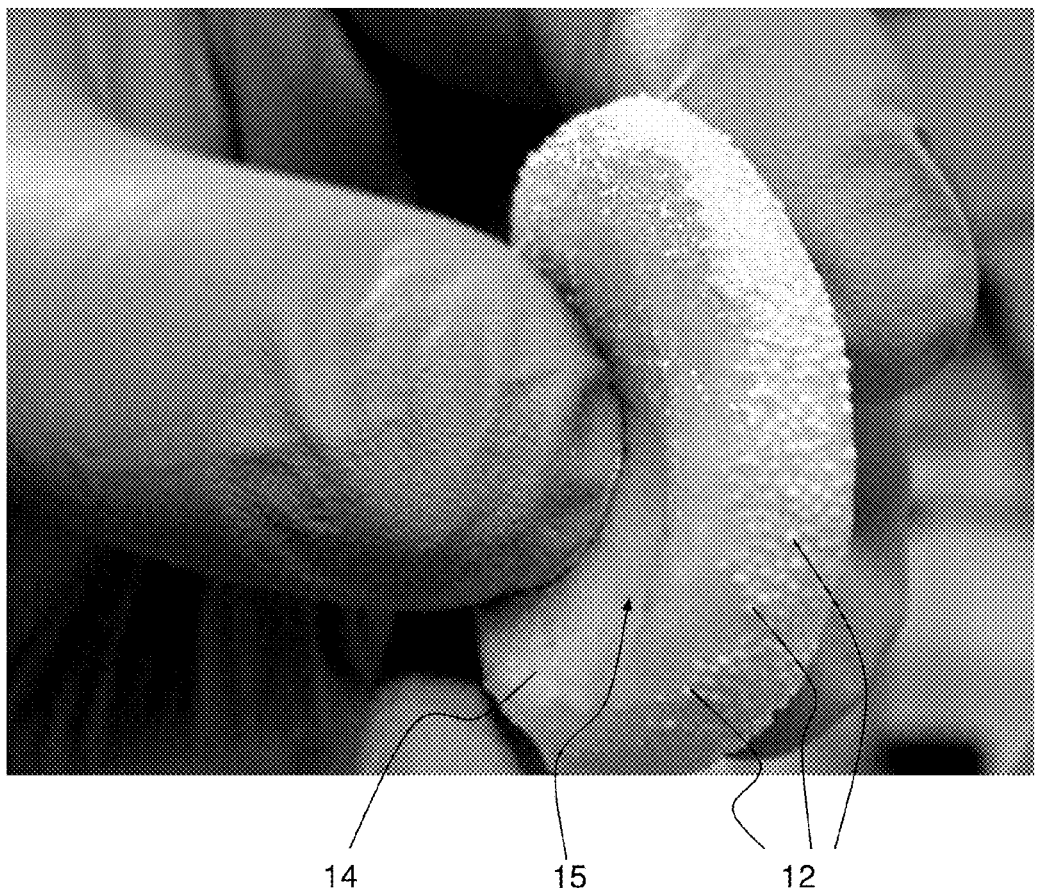
FIG. 2 is a reproduction of a photograph which shows a scaffold for regenerating osteochondral lesions, obtained with a composite of the invention.

In a second aspect, the invention relates to the scaffold obtained by means of the above-described method; an example of scaffold obtainable according to the invention is shown in FIG. 2, which depicts the reproduction of a photograph of a sample produced by the inventors and which highlights its elasticity. This scaffold 15 consists of a matrix of collagen chains entangled together to form the dehydrated hydrogel 14, which only in a part thereof incorporates the granules of HA/β-TCP 12. No chemical reaction occurs between collagen and HA/β-TCP of the granules in the product, but rather, only a purely physical interaction.

Therefore, the product is a scaffold for the regeneration of tissues for use in different areas of surgery, and in particular for the regeneration of bone and sub-chondral tissues in orthopedic field; this scaffold uses the known regenerative collagen properties and HA/β-TCP reconstructive properties, in the form of a biphasic matrix where the components are perfectly separated from each other, but at the same time integrated into each other. The product size may vary within wide ranges but in view of the intended uses as scaffolds for the insertion into bone or joint cavities, typically its thickness can range from 2 to 7 mm, preferably from 4 to 6 mm, while the thickness of each of the two component layers (layer of HA/β-TCP granules incorporated into the collagen matrix, and collagen-only layer) can range from 1 to 6 mm, preferably from 2 to 4 mm.

The product naturally retains the high biocompatibility and biodegradability features of the two component materials and is therefore especially recommended for orthopedic surgery.

Given the particular configuration thereof, the product of the invention allows, where there is a lesion affecting both the bone and the cartilage, the positioning of the scaffold with the part containing collagen only facing the lesion affecting the cartilage and the part containing the granules facing the bone lesion.

The mode of using the composite biomaterials of the invention in orthopedic surgery, which will be apparent to the surgeon, can be summarized as follows.

An access route to the damaged area of the joint must first be opened, e.g. arthroscopically (i.e. through some small holes into which the arthroscope and the ancillary instruments are introduced) or, in the case of larger lesions, through incision in the skin and in the tissues overlying the joint. These operations are normally carried out in the absence of blood flow in the limb to be operated, which is usually inhibited with a tight pressing band in proximal position.

The lesion area is then cleaned by carefully removing all the malacic cartilage up to preparing a healthy and consistent edge, with well-defined borders and a shape as regular as possible.

Afterwards, the bone tissue immediately beneath the removed cartilage layer is cleaned and gently removed, should it be in any way damaged or missing. This latter operation is also intended to stimulate the sub-chondral tissue: the bleeding caused by a small lesion already present, or even induced (Steadman technique), provides a bone marrow blood flow in the repair area which is known to be filled with active cells in tissue repair processes, such as, for example, mesenchymal stem cells, capable of differentiating into cells of new tissue, both bone and cartilaginous tissue.

Once the procedures for preparing the lesion area have been completed, the extent of the same is measured while maintaining the sterility of the site to be treated. A template is usually used, generally made of a malleable, sterile plastic material, or an equally sterile tin foil, having a size useful for detection, overlapping the template on the lesion and cutting the edges thereof over the contours of the lesion, so as to obtain a template having a shape and size matching as much as possible those of the osteochondral lesion to be covered.

With the sterile template thus obtained, the composite biomaterial of the invention is then cut, in a sterile environment, respecting the exact size of the lesion, so as to obtain a scaffold which is accurate and, most importantly, which is perfectly adhering to the edges of the lesion and which is equalized to the level of the surrounding cartilage, as much as possible, without interruption.

The scaffold thus obtained is then positioned so as to completely cover the lesion area previously prepared, making sure that the side with the prevalence of bone substitute (granules of HA/β-TCP) is facing the sub-chondral tissue, thus keeping the side consisting of collagen only positioned towards the joint space. In this step, it is important to ensure that the graft is well-leveled on the profile of the articular cartilage, without bumps or excessive depressions which would have a direct impact on the mobility of the joint and on the quality of the regenerated tissue. In order to fix the composite biomaterial in the area of the graft, it is preferable to use fibrin glue, to form a continuum between the healthy native tissue and the artificial biocomposite tissue, so as to allow the host cells to pass into the meshes of the composite scaffold, thus completing the colonization of the new cover tissue and stimulating the production of new extracellular matrix, both of the bone and of the cartilage tissue.

At the end of surgery, the tourniquet is removed to check the tightness of the graft just positioned into the lesion site and the kinematic efficiency of the joint; with the restoration of the blood stream, the material of the scaffold is soaked in the patient's bone marrow blood, thus creating a three-dimensional environment suitable for tissue regeneration.

Finally, the skin is sutured; the post-operative period usually requires absolute immobility, with the limb stretched, for at least 36 hours, after which the rehabilitation process can begin.

Other ways of using the biomaterials of the invention in other areas of surgery will be apparent to specialized surgeons.

The present invention will be further described by the following examples. In the examples, the amounts of the scaffold components are reported based on the size of the container where the mixing is made and based on the final thickness of the scaffold.

Example 1

Preparation of a Membrane Made of Collagen and Granules of HA/β-TCP, with a Final Thickness of 7 mm 16 grams of 1% collagen gel in aqueous solution are weighed in a glass container having dimensions of 5×5×2 cm. With the aid of a heating plate, the glass container containing the collagen solution is heated to 70° C. Using a probe thermometer, the temperature of the collagen solution is checked. When the collagen solution reaches a temperature of 62° C., it appears as a slightly viscous, slightly opalescent fluid. The heating plate is turned off and 5 grams of granules of HA/β-TCP, with a size of between 0.3 and 0.6 mm, are evenly distributed over the collagen solution surface. The granules settle, by gravity, on the bottom of the glass container forming a well-defined layer. The container is then stored at −30° C. for at least 24 hours. The frozen product is subjected to lyophilization. A composite material made of collagen/granules having a size of 4.5×4.5 cm with a thickness of 2 mm of collagen only and 5 mm of granules of HA/β-TCP in the collagen matrix is thus obtained.

Example 2

Preparation of a Membrane Made of Collagen and Granules of HA/β-TCP, with a Final Thickness of 5 mm 16 grams of 1% collagen gel in aqueous solution are weighed in a glass container having dimensions of 5×5×2 cm. With the aid of a heating plate, the glass container containing the collagen solution is heated to 70° C. Using a probe thermometer, the temperature of the collagen solution is checked. When the collagen solution reaches a temperature of 62° C., it appears as a slightly viscous, slightly opalescent fluid. The heating plate is turned off and 3 grams of granules of HA/β-TCP, with a size of between 0.3 and 0.6 mm, are evenly distributed over the collagen solution surface. The granules settle, by gravity, on the bottom of the glass container forming a well-defined layer. The container is then stored at −30° C. for at least 24 hours. The frozen product is subjected to lyophilization. A composite material of collagen/granules having a size of 4.5×4.5 cm with a thickness of 2 mm of collagen only and 3 mm of granules of HA/β-TCP in the collagen matrix is thus obtained.

Example 3

Preparation of a Membrane Made of Collagen and Granules of HA/β-TCP, with a Final Thickness of 6 mm 12.5 grams of 1% collagen gel in aqueous solution are weighed in a porcelain container having dimensions of 4.5×5×1.5 cm. With the aid of a heating plate, the porcelain container containing the collagen solution is heated to 70° C. Using a probe thermometer, the temperature of the collagen solution is checked. When the collagen solution reaches a temperature of 62° C., it appears as a slightly viscous, slightly opalescent fluid. The heating plate is turned off and 1.8 grams of granules of HA/β-TCP, with a size of between 0.3 and 0.6 mm, are evenly distributed over the collagen solution surface. The granules settle, by gravity, on the bottom of the porcelain container forming a well-defined layer. The container is then stored at −30° C. for at least 24 hours. The frozen product is subjected to lyophilization. A composite material of collagen/granules having a size of 3×4.5 cm with a thickness of 4 mm of collagen only and 2 mm of granules of HA/β-TCP in the collagen matrix is thus obtained.

Example 4

Preparation of a Membrane Made of Collagen and Granules of HA/β-TCP, with a Final Thickness of 5 mm 10.2 grams of 1% collagen gel in aqueous solution are weighed in a porcelain container having dimensions of 4.5×5×1.5 cm. With the aid of a heating plate, the porcelain container containing the collagen solution is heated to 70° C. Using a probe thermometer, the temperature of the collagen solution is checked. When the collagen solution reaches a temperature of 62° C., it appears as a slightly viscous, slightly opalescent fluid. The heating plate is turned off and 1.5 grams of granules of HA/β-TCP, with a size of between 0.5 and 1 mm, are evenly distributed over the collagen solution surface. The granules settle, by gravity, on the bottom of the porcelain container forming a well-defined layer. The container is then stored at −30° C. for at least 24 hours. The frozen product is subjected to lyophilization. A composite material of collagen/granules having a size of 3×4.5 cm with a thickness of 2 mm of collagen only and 3 mm of granules of HA/β-TCP in the collagen matrix is thus obtained.

Example 5

Preparation of a Membrane Made of Collagen and Granules of HA/β-TCP, with a Final Thickness of 6 mm 12.5 grams of 1% collagen gel in aqueous solution are weighed in a porcelain container having dimensions of 4.5×5×1.5 cm. With the aid of a heating plate, the porcelain container containing the collagen solution is heated to 70° C. Using a probe thermometer, the temperature of the collagen solution is checked. When the collagen solution reaches a temperature of 62° C., it appears as a slightly viscous, slightly opalescent fluid. The heating plate is turned off and 1.6 grams of granules of HA/β-TCP, with a size of between 0.5 and 1 mm, are evenly distributed over the collagen solution surface.

The granules settle, by gravity, on the bottom of the porcelain container forming a well-defined layer. The container is then stored at −20° C. for at least 24 hours. The frozen product is subjected to lyophilization. A composite material of collagen/granules having a size of 3×4.5 cm with a thickness of 3 mm of collagen only and 3 mm of granules of HA/β-TCP in the collagen matrix is thus obtained.

Example 6

Preparation of a Membrane Made of Collagen and Granules of HA/β-TCP, with a Final Thickness of 6 mm 360 grams of 1% collagen gel in aqueous solution are weighed in a steel container having dimensions of 35×35×5 cm. With the aid of a heating plate, the steel container containing the collagen solution is heated to 70° C. Using a probe thermometer, the temperature of the collagen solution is checked. When the collagen solution reaches a temperature of 62° C., it appears as a slightly viscous, slightly opalescent fluid. The heating plate is turned off and 52 grams of granules of HA/β-TCP, with a size of between 0.3 and 0.6 mm, are evenly distributed over the collagen solution surface. The granules settle, by gravity, on the bottom of the steel container forming a well-defined layer. The container is then stored at −30° C. for at least 24 hours. The frozen product is subjected to lyophilization. A composite material of collagen/granules having a size of 31×31 cm with a thickness of 4 mm of collagen only and 2 mm of granules of HA/β-TCP in the collagen matrix is thus obtained.

The invention claimed is:

1. Method for the production of a composite material consisting of hydroxyapatite and β-tricalcium phosphate in a collagen matrix, which comprises the following steps:
 a) preparing an aqueous solution consisting of water and collagen at a concentration of collagen between 0.5% and 2% by weight;
 b) distributing a layer of granules of hydroxyapatite β-tricalcium phosphate having a size between 0.3 and 5 mm on the surface of the aqueous solution prepared in step a) and waiting for deposition by gravity of said granules on the bottom of the layer of collagen solution, to produce a bottom layer consisting of hydroxyapatite/β-tricalcium phosphate and collagen and a top layer consisting of collagen;
 c) cooling the product obtained in step b) to a temperature between −20 and −30° C.; and
 d) subjecting to lyophilization the produce obtained in step c) to product said composite material.

2. Method according to claim 1, wherein said granules of hydroxyapatite/β-tricalcium phosphate contain between 50 and 70% by weight of hydroxyapatite.

3. Method according to claim 2, wherein said granules of hydroxyapatite/β-tricalcium phosphate contain about 60% by weight of hydroxyapatite.

4. Method according to claim 1, wherein the aqueous solution produced in step a) has a collagen concentration of about 1% by weight.

5. Method according to claim 1, wherein the aqueous solution of step a) is produced at a temperature between 60 and 65° C.

* * * * *